US00PP21926P2

(12) United States Plant Patent
Bradford

(10) Patent No.: US PP21,926 P2
(45) Date of Patent: May 24, 2011

(54) CHERRY TREE NAMED 'SWEET FRUITFUL'

(50) Latin Name: *Prunus avium*
Varietal Denomination: Sweet Fruitful

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/655,119

(22) Filed: Dec. 24, 2009

(51) Int. Cl.
*A01H 5/00* (2006.01)

(52) U.S. Cl. ..... Plt./181

(58) Field of Classification Search ..... Plt./181
See application file for complete search history.

(56) References Cited

U.S. PATENT DOCUMENTS

PP12,859 P2 8/2002 Bradford

*Primary Examiner* — Susan B McCormick Ewoldt

(57) ABSTRACT

The present invention relates to a cherry tree, *Prunus avium,* and more particularly to a new and distinct variety broadly characterized by a medium size, vigorous, hardy, self-fertile, very productive and regular bearing tree. The fruit matures under the ecological conditions described in the latter part of May, with first picking on May 23, 2009. The fruit is uniformly medium in size, sweet in flavor, somewhat oblate in shape, clingstone in type, firm in texture, red in flesh color, and full red in skin color.

1 Drawing Sheet

Botanical classification: *Prunus avium.*
Varietal denomination: 'SWEET FRUITFUL'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of cherry tree, which has been denominated varietally as 'SWEET FRUITFUL'.

During the spring of 2000 I gathered fruit from several different unnamed cherry seedlings in my experimental orchard near Le Grand, Calif. in Merced County (San Joaquin Valley). The seeds from this fruit were removed, cracked, stratified, germinated, and grown as seedlings on their own root in my greenhouse, and upon reaching dormancy transplanted to a cultivated area of my experimental orchard described above. During the fruit evaluation season of 2004 I selected the present variety as a single tree from the group described above. Subsequent to origination of the present variety of cherry tree, I asexually reproduced it by budding and grafting in the experimental orchard described above, and such reproduction of plant and fruit characteristics were true to the original plant in all respects. The reproduction of the variety included the use of 'Colt' (unpatented) rootstock, upon which the present variety was compatible and true to type.

The present variety is most similar to the 'Glenred' (U.S. Plant Pat. No. 12,859) cherry by producing cherries that are large in size, oblate in shape, firm in texture, dark red in skin color, red in flesh color, and sweet in flavor, but is distinguished therefrom by blooming about three days later, by being self-fruitful instead of self-sterile, and by producing cherries that ripen about seven days later.

SUMMARY OF VARIETY

In summary, the present variety is characterized by a medium size, vigorous, hardy, self-fertile, very productive and regular bearing tree. The fruit matures under the ecological conditions described in the latter part of May, with first picking on May 23, 2009. The fruit is uniformly medium in size, sweet in flavor, somewhat oblate in shape, clingstone in type, firm in texture, red in flesh color, and full red in skin color.

DRAWING

The accompanying photograph displays four fruits with the stems attached, two whole fruits detached from the stems to exhibit the skin color and form, one fruit sectioned to reveal the flesh and fibers, an individual stone, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of shipping ripe on May 25, 2009, on the original tree during its ninth growing season. All major color code designations are by reference to the Inter-Society Color Council, National Bureau of Standards. Common color names are also used occasionally.

Parentage

Seed parent: Unknown.
Pollen parent: Unknown.

Tree

Size: Medium, reaching a height of 18' [5.49 m.] and a spread of 10' [3.05 m.] after nine growing seasons.

Vigor: Vigorous, responding typically to irrigation and fertilization. The plant should be grown on a standard commercial rootstock for production purposes.

Growth: Upright and open.
Form: Central leader.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive.
Fertility: Self-fruitful.
Bearing: Regular bearer, with no crop failures observed.
Trunk:
*Size.*—Medium, reaching a maximum diameter of 4⅞" [124 mm.] after the ninth growing season.
*Texture.*—Shaggy, somewhat rough.
*Bark color.*—A Grayish yellowish brown [80. gy.yBr] and Dark grayish yellowish brown [81. d.gy.yBr] variegation.
*Lenticels.*—Approximate Number Per Square Inch: 4. Color: Deep orange [51. deep O]. Average Size: ½" [12.7 mm.]. Shape: Elongated, eye-shaped.
Branches:
*Size.*—Diameter of the first horizontal limb is 2⅛" [54 mm.] measured 12" from the central leader.
*Texture.*—Smooth on first and second year wood, increasing roughness with age.
*Color.*—1st Year Wood: Strong yellow green [117. s.YG]. Older Wood: A Deep brown [56. deep Br] and Grayish yellowish brown [80. gy.yBr] variegation.
*Lenticels.*—Number Per Square Inch: About 12 on second year wood. Color: Brownish orange [54. brO]. Size: ⅛" to 5/16" [3.2-8.0 mm.]. Shape: Eye-shaped.
Leaves:
*Size.*—Large. Average Length: 5⅜" [137 mm.]. Average Width: 2 5/16" [59 mm.].
*Arrangement.*—Alternate.
*Thickness.*—Medium.
*Form.*—Oval.
*Apex.*—Acuminate.
*Base.*—Rounded to obtuse.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Light yellow green [119. l.YG].
*Petiole.*—Average Length: 1¼" [31.8 mm.]. Average Thickness: 3/32" [2.4 mm.]. Color: Light yellow green [119. l.YG], often Very deep red [14. v.deep R] where exposed to direct sunlight.
*Stipules.*—Number: 2 per leaf at development stage. Average Length: ½" [12.7 mm.]. Color: Light yellow green [119. l.YG] becoming Moderate reddish Brown [43. m.rBr] with age.
*Glands.*—Number: Mostly 2 per leaf. Position: Alternately positioned on the petiole just below the leaf blade. Size: Medium. Form: Globose. Color: Pale yellow green [121. p.YG] becoming Dark pink [6. d.Pk] with age.
*Leaf buds.*—Pointed, medium.
Flower buds:
*Hardiness.*—Hardy, with respect to central California winters.
*Diameter.*—Typically 5/16" [7.9 mm.] 3 days before bloom.
*Length.*—Typically ⅝" [15.9 mm.] 3 days before bloom.
*Form.*—Free.
*Surface.*—Non-pubescent.
*Tip color.*—White [263. white].
Flowers: Perfect, complete, perigynous, usually a single pistil, typically about twenty stamens, five sepals and petal locations alternately positioned.
*Average flower diameter.*—1 5/16" [33.4 mm.].
*Number of petals.*—Usually five, very few have extra petals or fragments.
*Petal shape.*—Circular to slightly oval.
*Petal margin.*—Very wavy with occasional serrations.
*Average petal diameter.*—⅝" [15.9 mm.].
*Average petal length.*—11/16" [17.5 mm.].
*Petal apex.*—Rounded with a small notch on most.
*Petal base.*—Cuneate.
*Petal color.*—White [263. white].
*Anther color.*—Light yellow [86. l.Y].
*Stigma color.*—Light greenish yellow [101. l.gY].
*Sepal color.*—Strong reddish brown [40. s.rBr] over Strong yellow green [117. s.YG].
*Sepal length.*—¼" [6.4 mm.].
*Sepal width.*—3/16" [4.8 mm.].
*Average pistil length.*—⅝" [15.9 mm.].
*Average stamen length.*—9/16" [14.3 mm.].
*Fragrance.*—Moderate.
*Pollen production.*—Moderate.
*Bloom density.*—Heavy.
*Blooming period.*—Early, seven days before 'Bing' (unpatented).
*Onset of bloom.*—One percent on Mar. 13, 2009.
*Date of full bloom.*—Mar. 23, 2009.
*Duration of bloom.*—One to two weeks, dependent on ambient temperature.
*Number per cluster.*—Usually 2 to 10, 6 average.

Fruit

Maturity when described: Shipping ripe, May 25, 2009.
Date of first picking: May 23, 2009.
Date of last picking: May 30, 2009.
Size: Uniform, medium.
*Average diameter axially.*—1 1/16" [27.0 mm.].
*Average diameter across cheek plane.*—1 3/16" [30.2 mm.].
*Average diameter across suture plane.*—15/16" [23.8 mm.].
*Typical weight.*—0.35 ounces [9.9 grams].
Form: Uniform, symmetrical, somewhat oblate.
*Longitudinal section form.*—Oval to oblate.
*Transverse section through diameter.*—Elliptical.
Suture: An inconspicuous line located in a shallow trough, extending from the base to the pistil point.
Ventral surface: Rounded, lipped slightly on both sides.
Lips: Equal.
Cavity: Flaring, rounded, suture showing on one side.
*Depth.*—⅛" [3.2 mm.].
*Breadth.*—9/16" [14.3 mm.].
Base: Slightly truncate if viewed in the suture plane, cordate if viewed parallel to the suture.
Apex: Rounded to slightly cordate.
Pistil point: An inconspicuous dot.

Stem: Medium.
*Average length.*—1⅜" [34.9 mm.].
*Average width.*—3/32" [2.4 mm.].
Skin:
*Thickness.*—Medium.
*Surface.*—Smooth.
*Tenacity.*—Tenacious to the flesh.
*Astringency.*—Slight.
*Tendency to crack.*—Less than average in rainy conditions, rare in dry seasons.
*Color.*—A Very dark purplish red [260. v.d.pR] smoothly blending into a Deep red [13. deep R].
Flesh:
*Color.*—Very dark purplish red [260. v.d.pR] near the skin and stone, Deep red [13. deep R] between.
*Surface of pit cavity.*—Covered with Very dark red [17. v.d.R] broken fibers when twisted away from the stone.
*Amygdalin.*—Moderate.
*Juice.*—Abundant, rich.
*Juice color.*—Deep red [13. deep R].
*Texture.*—Firm, crisp, melting.
*Fibers.*—Abundant, fine, tender.
*Ripens.*—Fairly even, slightly earliest at apex.
*Flavor.*—A tasty balance of acid and sugar, typically 18-22 brix.
*Aroma.*—Slight.
*Eating quality.*—Excellent.

STONE

Type: Clingstone.
Form: Oval.
Hilum: Narrow, oblong.
Base: Straight, somewhat truncate.
Apex: Rounded.
Sides: Equal.
Surface: Fairly smooth.
External color of stone: Light yellowish brown [76. l.yBr] when first removed.
Pit wall color when cracked: Pale orange yellow [73. p.OY].
Cavity surface color: Yellowish white [92. yWhite].
Average pit wall thickness: 1/16" [1.6 mm.]
Average width: 5/16" [7.9 mm.].
Average length: 7/16" [11.1 mm.].
Average breadth: ¼" [6.4 mm.].
Tendency to split: None.
Kernel:
*Form.*—Oval.
*Skin color.*—Pale yellow [89. p.Y] when first removed.
*Pellicle color.*—Grayish yellow [90. gy.Y].
*Vein color.*—Grayish yellow [90. gy.Y].
*Taste.*—Bitter.
*Viable.*—Yes.
*Average width.*—3/16" [4.8 mm.].
*Average length.*—¼" [6.4 mm.].
*Amygdalin.*—Abundant.

Use

Market: Fresh market and long distance shipping.
Keeping quality: Good, fruit quality observed to remain in good condition after 21 days in standard cold room at 34° Fahrenheit [1° Celsius].
Shipping quality: Good.
Resistance to insects: No unusual susceptibilities noted.
Resistance to diseases: No unusual susceptibilities noted.

Other Notes

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and described, that is most similar to the 'Glenred' (U.S. Plant Pat. No. 12,859) cherry by producing cherries that are large in size, oblate in shape, firm in texture, dark red in skin color, red in flesh color, and sweet in flavor, but is distinguished therefrom by blooming about three days later, by being self-fruitful instead of self-sterile, and by producing cherries that ripen about seven days later.

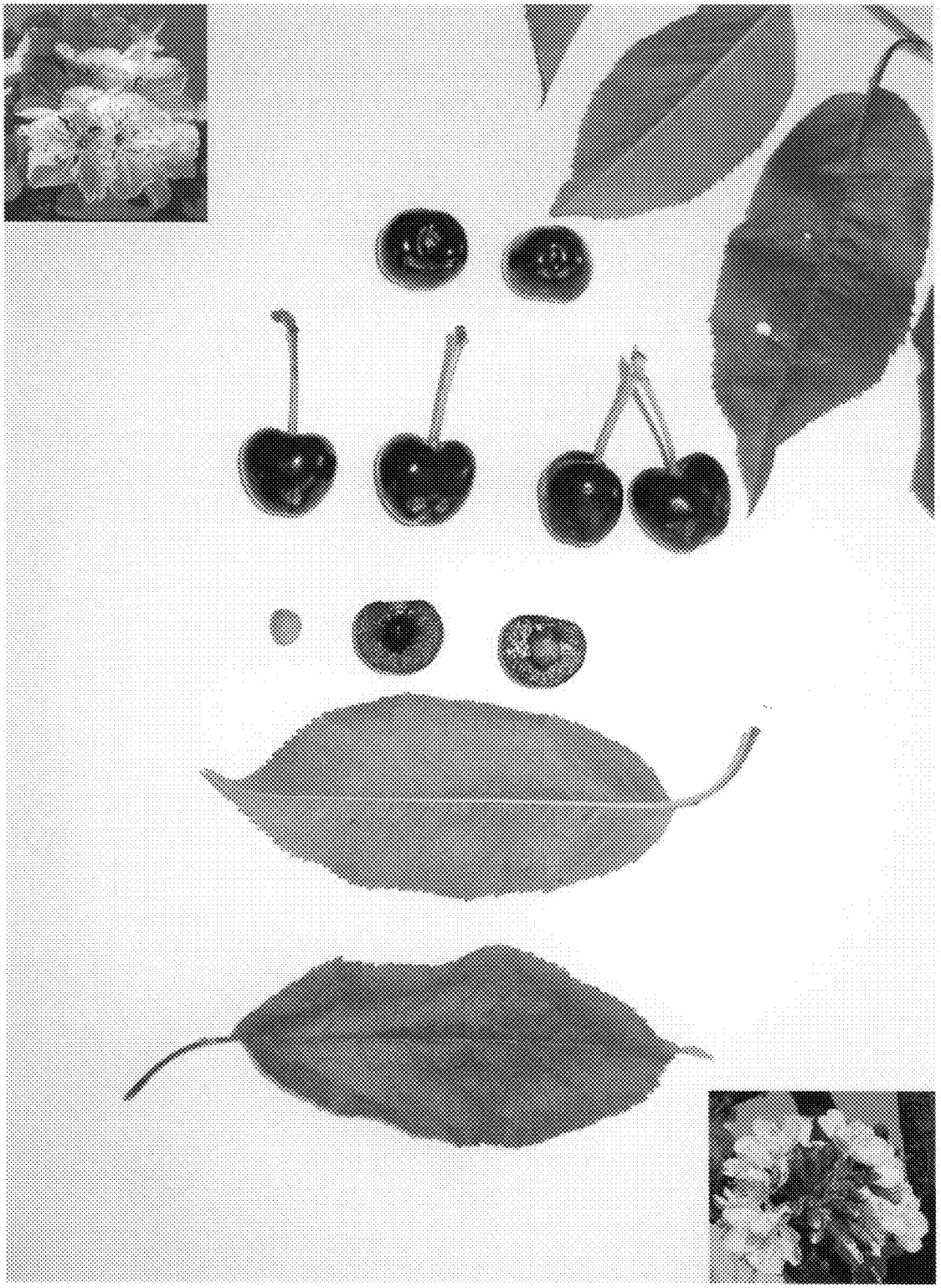

* * * * *